United States Patent
Pavlovsky (10) Patent No.: US 7,647,813 B2
(45) Date of Patent: Jan. 19, 2010

(54) HYDROGEN SENSOR

(75) Inventor: Igor Pavlovsky, Cedar Park, TX (US)

(73) Assignee: Applied Nanotech Holdings, Inc., Austin, TX (US)

( * ) Notice: Subject to any disclaimer, the term of this patent is extended or adjusted under 35 U.S.C. 154(b) by 160 days.

(21) Appl. No.: 11/524,698

(22) Filed: Sep. 21, 2006

(65) Prior Publication Data

US 2007/0068493 A1 Mar. 29, 2007

Related U.S. Application Data

(60) Provisional application No. 60/719,548, filed on Sep. 22, 2005.

(51) Int. Cl.
*G01N 7/00* (2006.01)
(52) U.S. Cl. .................. 73/24.01; 73/23.31; 73/24.06; 73/31.01; 73/31.02; 73/31.03; 73/31.05
(58) Field of Classification Search .......... 73/23.2, 73/23.31, 24.01, 24.06, 31.01, 31.02, 31.03, 73/31.05
See application file for complete search history.

(56) References Cited

U.S. PATENT DOCUMENTS

| 3,672,388 | A | | 6/1972 | Ringwall et al. | |
|---|---|---|---|---|---|
| 3,864,628 | A | * | 2/1975 | Klass et al. | 324/71.1 |
| 4,222,045 | A | * | 9/1980 | Cholin | 340/628 |
| 4,760,351 | A | * | 7/1988 | Newell et al. | 331/48 |
| 4,782,334 | A | | 11/1988 | Meaney | |
| 5,014,908 | A | | 5/1991 | Cox | |
| 6,029,500 | A | | 2/2000 | Tom | |
| 6,494,079 | B1 | * | 12/2002 | Matsiev et al. | 73/24.05 |
| 6,905,655 | B2 | | 6/2005 | Gabriel et al. | |
| 6,997,039 | B2 | * | 2/2006 | Rao et al. | 73/24.06 |
| 7,146,857 | B2 | * | 12/2006 | Hok | 73/579 |
| 2004/0074303 | A1 | | 4/2004 | Matsiev et al. | |
| 2005/0007002 | A1 | * | 1/2005 | Golovchenko et al. | 313/311 |

OTHER PUBLICATIONS

Chopra, S. et al., "Carbon-Nanotube-Based Resonant-Circuit Sensor for Ammonia", Applied Physics Letters, vol. 80, No. 24, Jun. 17, 2002, pp. 4632-4634.*
Pham, A., "Carbon-Nanotube Resonator Sensors for Remote Sensing Systems", IEEE, 2003, pp. 1-3.*
Huang, X. M. H. et al., "Nanomechanical Hydrogen Sensing", Applied Physics Letters, vol. 86, No. 143104, 2005, pp. 143104-1 through 143104-3.*
Chopra, S. et al., "Gas Sensing Using Carbon Nanotube-Based Resonator", IEEE, 2004, pp. 399-402.*
Kong, J. et al., "Functionalized Carbon Nanotubes for Molecular Hydrogen Sensors", Adv. Mater., vol. 13, No. 18, Sep. 14, 2001, pp. 1384-1386.*
Qi, P. et al., "Toward Large Arrays of Multiplex Functionalized Carbon Nanotube Sensors for Highly Sensitive and Selective Molecular Detection", Nano Letters, vol. 3, No. 3, Feb. 6, 2003, pp. 347-351.*

* cited by examiner

*Primary Examiner*—Daniel S Larkin
(74) *Attorney, Agent, or Firm*—Kelly Kordzik; Matheson Keys Garsson & Kordzik PLLC (57) ABSTRACT

A hydrogen sensor (100) with instant response that uses one or more quartz tuning forks (101, 102) while no chemical reactions or other material modifications are involved. Sensor (100) can be used in any application to measure percent range of hydrogen concentrations.

11 Claims, 7 Drawing Sheets

HYDROGEN SENSOR

This application claims priority to U.S. Provisional Patent Application Ser. No. 60/719,548, filed Sep. 22, 2005.

TECHNICAL FIELD

This invention relates to gas sensors, and more particularly to hydrogen sensors.

BACKGROUND

There are many technologies for sensing hydrogen, some of them are commercialized. Most of the technologies can be split into two categories—chemical sensors and palladium-based sensors. They use properties of hydrogen to interact with materials, either via chemical reactions as in metal oxide sensors, or by dissolving in Pd and changing the physical properties of Pd—H system. The property of Pd to dissolve and store hydrogen is implemented in many approaches to designs of the sensors, including quartz microbalance sensors, which detect a change in resonance oscillation frequency as the palladium film changes its mass while it absorbs hydrogen. A related patent is U.S. Pat. No. 6,029,500. However, using palladium or similar hydrogen dissolving metals as active coatings results in poor stability of the devices as the metal surface oxidizes with time, and also in case of Pd, it can be poisoned by sulfur or delaminated due to the phase change occurring at high hydrogen concentrations. Thus, it is desired to have a sensor stable in time at various chemical and physical conditions.

DESCRIPTION OF DRAWINGS

Like reference symbols in the various drawings indicate like elements.

DETAILED DESCRIPTION

Hydrogen is known as the element with the smallest atomic mass. In a gas mixture in thermodynamic equilibrium, molecules have a mean energy of ~3/2 kT, whether they are molecules of hydrogen, nitrogen, oxygen, etc. The momentum of a molecule is mv, where m is molecular mass, and v is the mean molecular velocity equal to $(8\,kT/\pi m)^{1/2}$. So, the momentum of a gas molecule at a given temperature will depend on its mass as $(m)^{1/2}$. The difference in momentum and size (effective diameter) of molecules leads to the difference in other macroscopic parameters of gases, such as viscosity and diffusion rate.

During oscillations in a gas environment, a vibrating object, such as tuning fork, tines impart momentum to gas molecules resulting in mechanical energy loss in the tines. This loss causes a change in the resonant oscillation frequency of the fork, and the frequency shift will depend on a momentum that the tines impart to gas molecules. This means that in a gas that contains light molecules, such as hydrogen, the losses due to interaction with the gas molecules will be less than in an environment without hydrogen. Hence, the frequency of oscillations will be higher in an environment having a presence of hydrogen.

In a tuning fork quartz oscillator, the fork tines symmetrically vibrate in an antiphase flexure mode, wherein the tines move in opposite directions against each other at any moment in time. The speed at which the tines oscillate can be estimated as follows. The amplitude of the tine deflection is approximately 60 nm/V. If the driving voltage on the tines is about 1V, then at a frequency of 32768 Hz, the tines will have a characteristic speed of ~2 mm/sec. That is much less than the speed of gas molecules (hundreds of meters per second), and it is possible to consider a quasi-static case for this interaction. Therefore, it is mostly the macroscopic characteristics of gases that will affect tuning fork oscillation frequency.

The described tuning fork sensor is not selective to hydrogen, and other light gases like, helium, may interfere with the H2. To avoid interference, it is possible to use H2-permeable membranes, like Pd (palladium) membranes, to improve selectivity.

The frequency change in the tuning fork resonator is usually small, so a differential frequency detection method may be used for the detection of small frequency deviations.

Along with frequency, the quality factor Q and the electric impedance of the tuning fork resonator changes as the oscillation energy is dissipated in gas environment.

Figure 1:
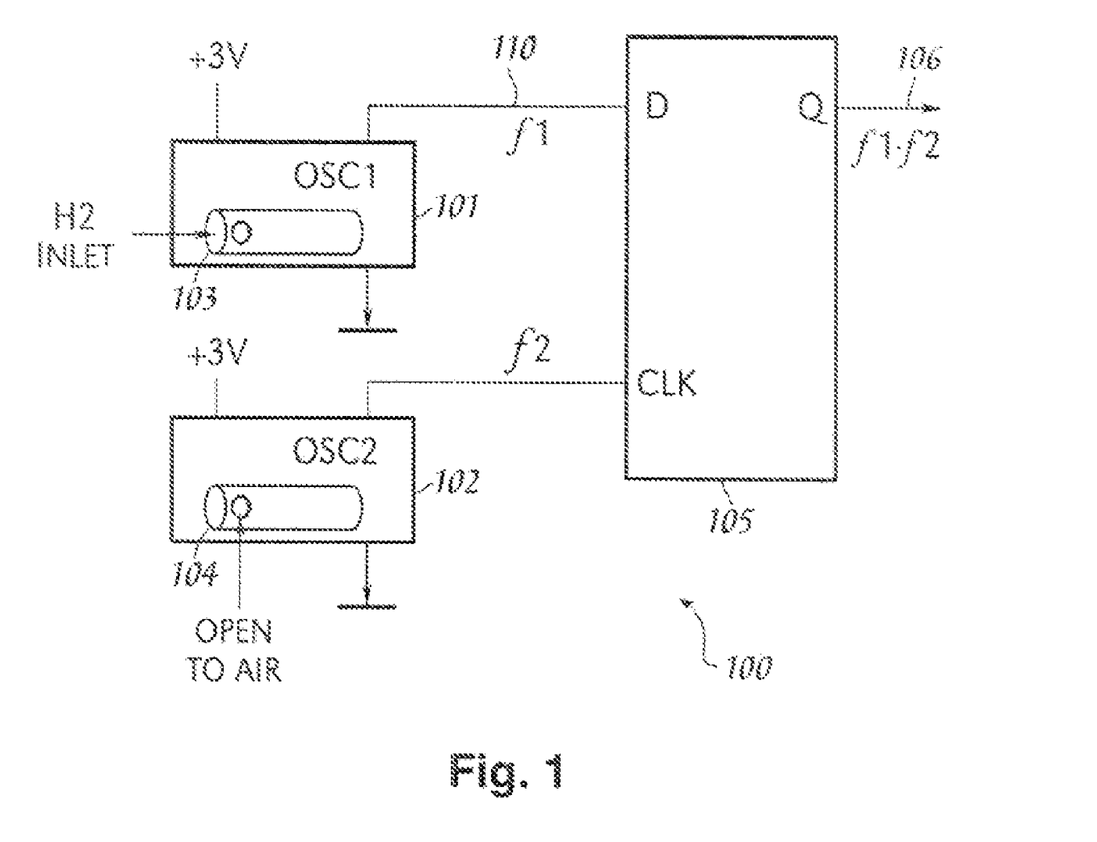
FIG. 1 illustrates an embodiment of the present invention.

Referring to FIG. 1, embodiments of the present invention illustrate two ECS-327SMO type oscillators 101, 102 which may be used for gas detection. The tuning fork oscillator cans' tops 103, 104 are sanded off for access of gas, and the oscillators' outputs 110, 111 are connected to D and CLK inputs of a D flip-flop trigger 105. The primary oscillator (OSC1) 101 is located in a suspected hydrogen-containing gas environment. The reference oscillator (OSC2) 102 is used to account for changes in gas composition (such as humidity changes) and for temperature compensation. The frequency of the primary oscillator 101 will increase with the hydrogen concentration. The frequency difference at the flip-flop output 106 is thus proportional to the hydrogen concentration.

The sensor 100 may be characterized using hydrogen gas mixed with air at volume concentrations of 0 to 16% at room temperature. The hydrogen-air mixture may be prepared using two 100 sccm mass flow controllers. The interval between the frequency beats may be measured using a Tektronix CDC250 counter.

Figure 2:
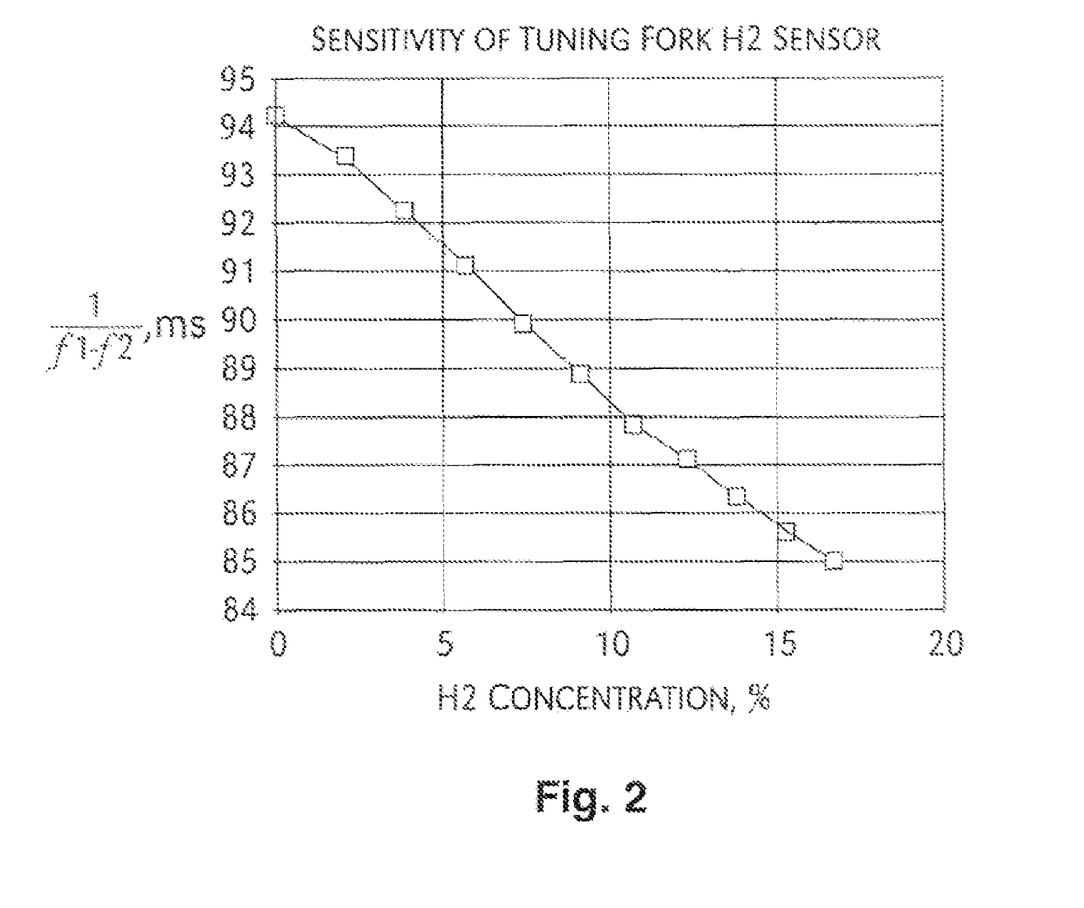
FIG. 2 illustrates a graph of sensitivity of a sensor configured in accordance with an embodiment of the present invention.

The response of the sensor 100 to hydrogen is quite linear in all ranges of concentrations. As can be seen in FIG. 2, a 9% change in the differential frequency may be observed when 16% $H_2$ concentration is achieved in the chamber of oscillator 101.

Figure 3:
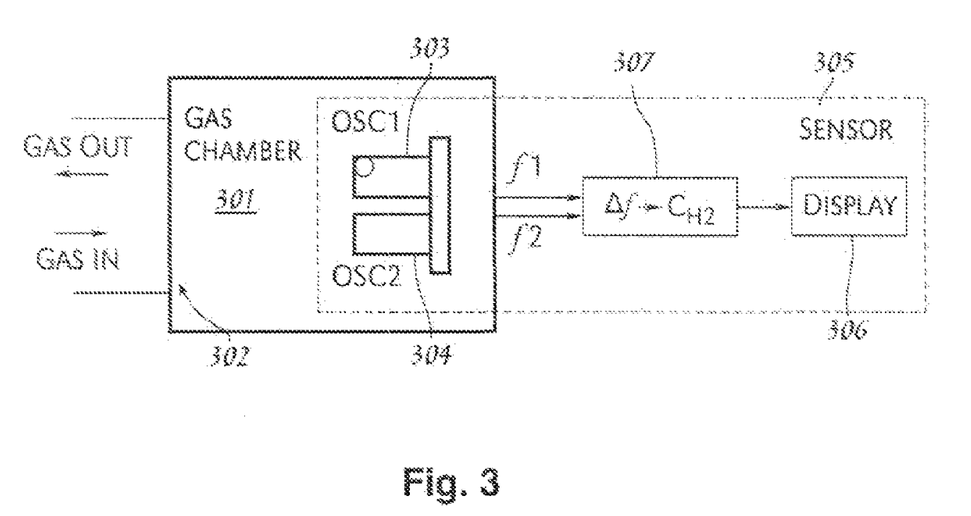
FIG. 3 illustrates another embodiment of the present invention.

FIG. 3 illustrates an alternative embodiment where two oscillators 303, 304 can make a sensor device 300 and be used to detect hydrogen in a gas chamber 301. Sensor 300 has the reference oscillator 304 sealed (the can's top is not sanded off) to protect from access to hydrogen. Along with the open oscillator 303 they can be placed into the measured gas environment next to each other. As noted above, an $H_2$-permeable membrane 302 may be used. In this embodiment, cross-compensation can be done for the temperature, but not for humidity changes. Sensor 300 comprises circuitry 307 for converting the difference in frequencies to an output parameter 305

(e.g., a number or voltage level) proportional to the concentration of hydrogen $C_{H2}$, and a display 306 for presenting the output parameter 305.

The concentration of hydrogen can then be calculated as follows:

$$f_1 = f_{10} + kC_{H2},$$

$$f_2 = f_{10} + f_{12},$$

$$\Delta f = f_1 - f_2 = f_{10} + kC_{H2} - f_{10} + f_{12} = kC_{H2} + f_{12},$$

where $f_{10}$ is the frequency of oscillator OSC1 303 without hydrogen, $f_{12}$ is the difference between the frequencies of OSC1 303 and OSC2 304 without hydrogen, k is the proportionality factor, and $C_{H2}$ is the concentration of hydrogen. The last expression can be recalculated as follows:

$$C_{H2} = (\Delta f - f_{12})/k.$$

Figure 4:
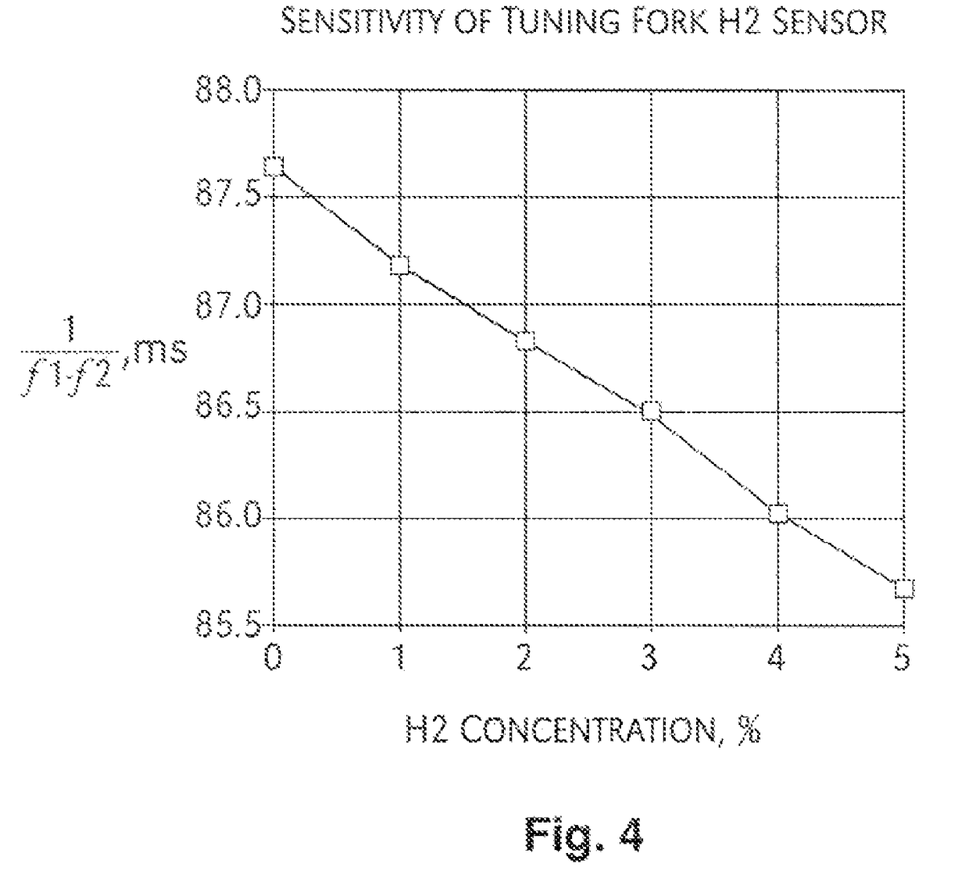
FIG. 4 illustrates a graph of sensitivity of a sensor configured in accordance with an embodiment of the present invention.

Test results for sensor 300 with sealed and open can oscillators are shown in FIG. 4. The sensor 300 was tested at room temperature, the flow rate of nitrogen was 200 sccm, and the flow rate of hydrogen changed from 0 to 10 sccm. The sensor 300 shows a near linear response to $H_2$ concentration changes.

Figure 5:
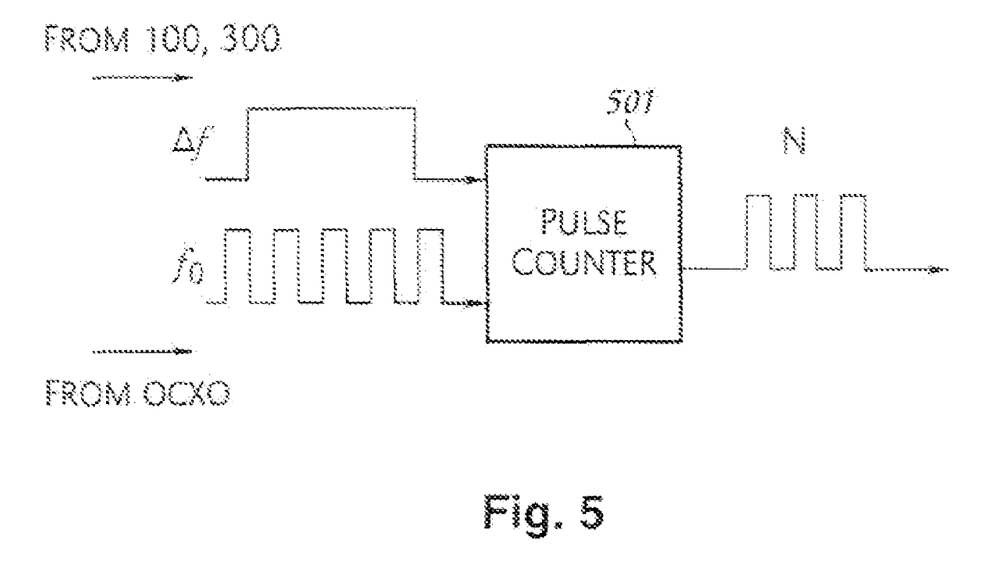
FIG. 5 illustrates a circuit for outputting results of embodiments of the present invention.

Referring to FIG. 5, since a difference in frequencies of two oscillators can be as small as several Hz, it may be more convenient to measure time intervals between two frequency beating pulses. In this case, a separate high-frequency oscillator (not shown) can be used to fill the time intervals with pulses at a fixed frequency $f_0$. For precision measurements, oven-controlled crystal oscillators (OCXO) can be used to generate such pulses. The time interval between the frequency beatings will be $$T = 1/\Delta f = 1/(f_1 - f_2) = 1/(kC_{H2} + f_{12}).$$

If the OCXO stabilized generator has a frequency of $f_0$, then the number of pulses at the output N of pulse counter 501 will be $$N = f_0 T = f_0/\Delta f = f_0/(kC_{H2} + f_{12}).$$

In another embodiment, a device for measuring oscillation parameters of the tuning fork detects changes in Q factor and an impedance of the tuning fork as hydrogen will change the energy that is dissipated by the tuning fork tines. The energy dissipation in the tuning fork can be described as follows.

If a mechanical system such, as a tuning fork, has a mechanical resistance $R_M$, the quality factor Q at a resonant frequency $f_0$ will be $$Q \sim f_0/R_M.$$

The mechanical resistance $R_M$ is a function of the gas viscosity V, and thus $R_M$ can be described as the following series:

$$R_M = R_{M0}(1 + c_1 V + c_2 V^2 + \ldots)$$

where c1, c2, . . . , are the proportionality coefficients. For media with low viscosity, such as a gas, this can be rewritten as $$R_M = R_{M0}(1 + c_1 V)$$

where $R_{M0}$ is the mechanical resistance in vacuum and does not depend on a gas viscosity.

Hydrogen has approximately two times lower viscosity than air ($8.4 \times 10^{-6}$ Pa*s vs. $17.4 \times 10^{-6}$ Pa*s at 0° C.), and, hence, the mechanical resistance will decrease at higher relative hydrogen concentrations. Thus:

$$R_M = R_{M0}(a - bC_{H2}),$$

where a and b are functions of viscosities of hydrogen and a balanced gas (such as air), and $C_{H2}$ is a relative concentration of hydrogen in the gas mixture. Then the concentration can be defined as $$C_{H2} \sim (a - f_0/QR_{M0})/b$$

where Q can be measured experimentally. The quality factor can be easily found when the quartz tuning fork is a part of an electrical circuit, since, by definition, $$Q = f_0/\Delta f.$$

Measuring $\Delta f$ can be done by conventional methods used in electronics (frequency sweeping around $f_0$, measuring amplitude attenuation of oscillation pulses (damping factor), etc.). Since the electric impedance is also a function of the quality factor, $$|Z(\omega)|^2 \sim (1/Q^2 - 1) + (\omega/\omega_0)^2 + (\omega_0/\omega)^2,$$

it can be used for determination of hydrogen concentration as well.

Figure 6:
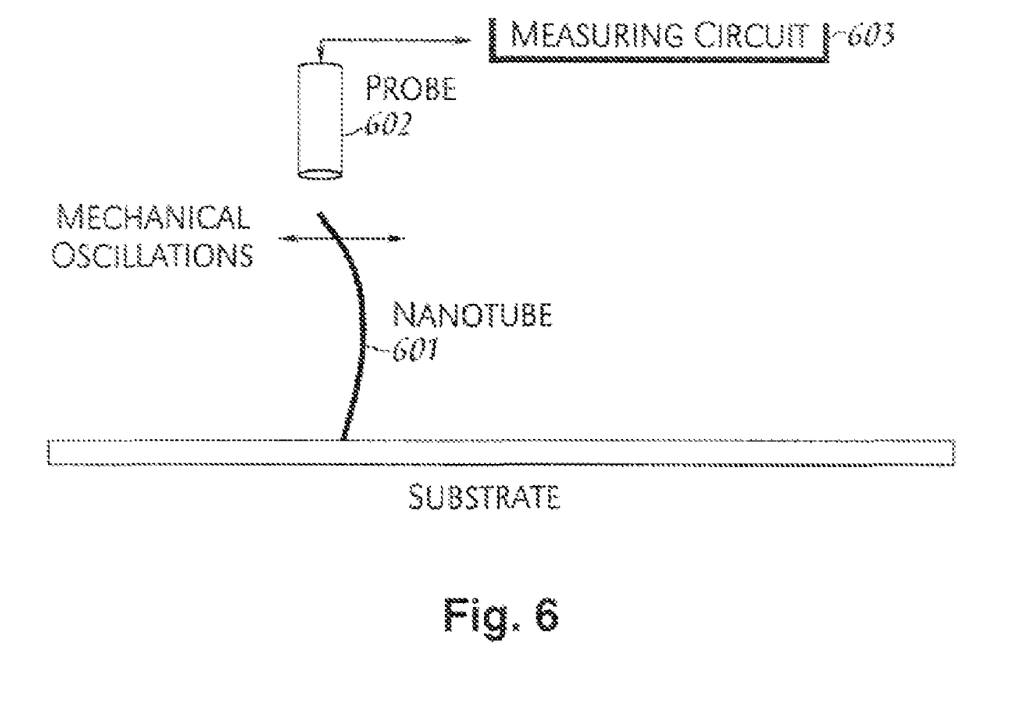
FIG. 6 illustrates another embodiment of the present invention.

Referring to FIG. 6, another embodiment is based on measurements of the frequency and/or the Q factor of a periodic movement (vibration) of a nanowire or a nanotube 601, such as a carbon nanotube, in flexure mode. The measurement system 603 of the sensor will include a means to detect and quantify such oscillations. An example of a system that is electrically coupled to a nanotube 601 is shown in FIG. 6. Nanotube 601 vibrates due to an applied external force (not shown), such as mechanical or electrostatic force. An electric probe 602 coupled to the nanotube 601 either by field electron emission to/from the nanotube 601, or through the capacitance between the nanotube 601 and the probe 602, or by any other coupling mechanism that is known to one skilled in the art. The probe 602 forms a part of the measuring electric circuit 603 that can measure deviations in coupling parameters (such as capacitance) and determine the frequency of these deviations. Details of such a measuring circuit are not described, but would be within the capability of one skilled in the art.

As described above, the vibration frequency of the nanotube 601 or nanowire will depend on the viscosity of a surrounding gas, which, in turn, will depend on the concentration of hydrogen in the gas.

Figure 7:
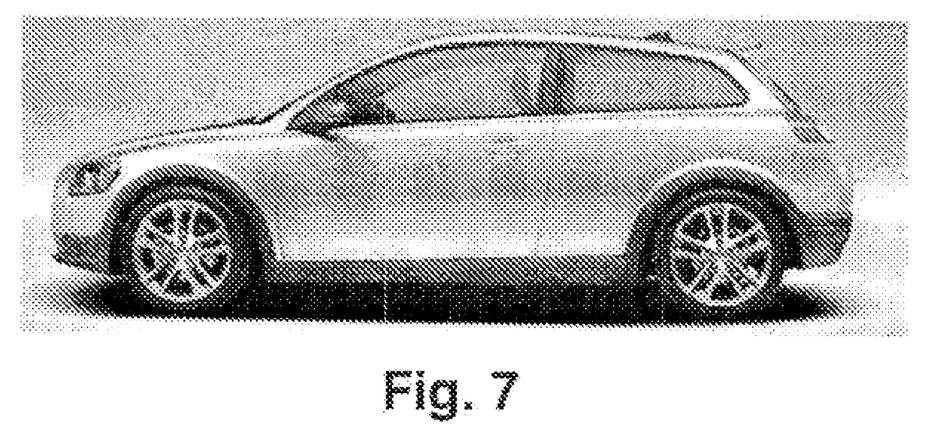
FIG. 7 illustrates an exemplary application of embodiments of the present invention.

The sensitivity range of the sensor is 0 to 100% $H_2$, with a detectivity limit of at least 1%, as can be seen from the sensitivity graphs shown above in FIGS. 2 and 4. The lower flammability level of hydrogen is 4%, and lower explosive limit (LEL) is 17%. Thus, the described sensors may be used as a leak detector for many applications. For example, referring to FIG. 7, in a fuel cell powered car, the sensor can be installed near the fuel cell reactor, near the passenger seats, or in the exhaust system.

An LEL detector that uses the described sensor may be a portable handheld device, with a sensor incorporated in the device body, or placed at the end of an attachable sampling probe. The device may have indications of concentration on a display along with a sound alarm if the concentration of hydrogen reaches a certain critical level. Other applications include water electrolysers, hydrogen storage systems, industrial equipment, etc.

Improvements can be made to stabilize the sensor response against temperature, humidity, atmospheric pressure, quartz aging, and other conditions of operation.

A number of embodiments of the invention have been described. Nevertheless, it will be understood that various modifications may be made without departing from the spirit and scope of the invention.

What is claimed is:

1. A gas sensor comprising:
   a first electro-mechanical oscillator having a first frequency output controlled by a first mechanically resonant element;
   a second electro-mechanical oscillator having a second frequency output controlled by a second mechanically resonant element, wherein the first mechanically resonant element exposed to a first environment that may contain a gas to be sensed, and the second mechanically resonant element exposed to a second environment that does not contain the gas to be sensed; and
   circuitry for determining if the gas is present in the first environment by producing a sense signal with a frequency value that is a frequency difference between the first and second frequency outputs, wherein the gas is hydrogen and a presence of hydrogen in the first environment causes the first mechanically resonant element to vibrate at a higher frequency.

2. The gas sensor as recited in claim 1 wherein the determining circuit is a D flip-flop having its D input coupled to the first frequency output and its clock input coupled to the second frequency output so that a Q output of the D flip-flop produces the sense signal.

3. The gas sensor as recited in claim 1, further comprising a means to activate both the first and second mechanically resonant elements of the first and second oscillators.

4. The gas sensor as recited in claim 1, wherein the gas to be sensed is introduced to the first environment through a membrane preferentially permeable to the gas to be sensed.

5. The gas sensor as recited in claim 1, further comprising a pulse counter having one input receiving the sense signal and another input receiving a reference frequency signal and an output generating a number of pulses proportional to a concentration of the gas in the first environment.

6. A gas sensor comprising:
   means for activating a mechanical vibration to an oscillating rod thereby causing the mechanical vibration in the oscillating rod to occur at a natural oscillating frequency;
   means for measuring a change in the natural oscillating frequency of the oscillating rod; and
   means for outputting a sensing signal when the measuring means detects the change in the natural oscillating frequency in response to exposing the oscillating rod to an environment containing a particular gas, wherein the oscillating rod does not absorb gases when in the environment.

7. The gas sensor as recited in claim 6, wherein the oscillating rod comprises a carbon nanotube.

8. The gas sensor as recited in claim 6, wherein the oscillating rod is a tuning mechanism for an oscillator.

9. The gas sensor as recited in claim 8, wherein the measuring means comprises a flip-flop circuit.

10. A gas sensor comprising:
    a first oscillator having a first frequency output;
    a second oscillator having a second frequency output, the first oscillator exposed to an environment that may contain a gas to be sensed, and the second oscillator exposed to an environment that does not contain the gas to be sensed; and
    circuitry for determining if the gas is sensed by the first oscillator by producing a frequency signal that is a difference between the first and second frequency outputs, wherein the gas is hydrogen, and wherein a presence of hydrogen sensed by the first oscillator will cause it to vibrate at a higher frequency.

11. A gas sensor comprising:
    a first oscillator having a first frequency output;
    a second oscillator having a second frequency output, the first oscillator exposed to an environment that may contain a gas to be sensed, and the second oscillator exposed to an environment that does not contain the gas to be sensed;
    circuitry for determining if the gas is sensed by the first oscillator by producing a frequency signal that is a difference between the first and second frequency outputs; and
    a pulse counter having one input receiving the difference frequency signal and another input receiving a reference frequency signal to therefore output a number of pulses representing the sensing of the gas.

* * * * *